United States Patent [19]

Gremel et al.

[11] Patent Number: 4,568,367
[45] Date of Patent: Feb. 4, 1986

[54] BLOOD DEFOAMER WITH IMPROVED LIQUID SEAL

[75] Inventors: Robert F. Gremel; Kenneth M. Galt, both of Huntington Beach, Calif.

[73] Assignee: Shiley Incorporated, Irvine, Calif.

[21] Appl. No.: 441,464

[22] Filed: Nov. 15, 1982

[51] Int. Cl.[4] .............................................. B01D 19/02
[52] U.S. Cl. ..................................... 55/178; 210/188; 210/338; 210/342; 210/450; 210/927; 55/87; 128/DIG. 3; 422/47
[58] Field of Search ...................... 210/188, 315, 323.2, 210/338, 342, 453, 927, 450; 55/471, 178, 87; 128/DIG. 3; 422/47

[56] References Cited

U.S. PATENT DOCUMENTS

| | | | |
|---|---|---|---|
| 1,710,758 | 4/1929 | Wright | 210/342 |
| 2,598,322 | 5/1952 | Vokes | 210/342 |
| 3,768,977 | 10/1973 | Brumfield et al. | 128/DIG. 3 |
| 3,807,958 | 4/1974 | Brumfield et al. | 128/DIG. 3 |
| 4,033,724 | 7/1977 | Tamiya | 128/DIG. 3 |
| 4,065,264 | 12/1977 | Lewin | 128/399 X |
| 4,138,288 | 2/1979 | Lewin | 422/46 X |
| 4,138,464 | 2/1979 | Lewin | 128/DIG. 3 X |
| 4,157,965 | 6/1979 | Raible | 210/305 |
| 4,231,988 | 11/1980 | Kurata | 128/DIG. 3 |
| 4,240,409 | 12/1980 | Robinson et al. | 128/DIG. 3 |
| 4,374,088 | 2/1983 | Stenberg et al. | 261/DIG. 28 |

Primary Examiner—Barry S. Richman
Assistant Examiner—Titus B. Ledbetter, Jr.
Attorney, Agent, or Firm—Charles J. Knuth; Peter C. Richardson; Lawrence C. Akers

[57] ABSTRACT

A blood defoamer for use in surgical procedures is disclosed comprising a porous defoaming element, a non-porous end piece in contact with a surface of the defoaming element, and a layer of fabric affixed to the end piece adjacent to said surface. Bypass of blood flow around the layer of fabric, which is situated downstream of the defoaming element, and accumulation of bubbles in the defoamed blood reservoir are prevented by bonding a suitably configured retaining ring to the end piece with a portion of the layer of fabric held in a fluid-tight seal between the end piece and the retaining ring.

5 Claims, 3 Drawing Figures

BLOOD DEFOAMER WITH IMPROVED LIQUID SEAL

BACKGROUND OF THE INVENTION

Extracorporeal circulation of blood has been performed in surgical procedures such as open heart surgery for many years. An important component in the extracorporeal blood circuit is a blood oxygenator. The function of the oxygenator is to place oxygen in close relationship to the venous blood so that the oxygen reacts with the hemoglobin with resultant absorption of the oxygen and release of carbon dioxide.

Various types of blood oxygenators are in use. Among the most popular is the type known as the "bubble oxygenator" wherein bubbles of oxygen are introduced directly into the blood. One consequence of using a bubble oxygenator is that once the blood has been arterialized by the introduction of oxygen bubbles, these bubbles must be removed from the blood before the blood is returned to the patient's body, since the presence of gaseous bubbles in the patient's bloodstream can be injurious and substantial amounts of bubbles may lead to death. Therefore, bubble oxygenators typically incorporate some sort of defoaming means which collapses the bubbles in the blood, thereby separating the residual oxygenating gas from the liquid arterialized blood before the blood is reintroduced to the patient.

One type of bubble oxygenator with defoaming means, which has been employed with highly successful results for several years, is disclosed in U.S. Pat. Nos. 4,065,264; 4,138,288 and 4,138,464. In this type of device, the defoaming element is an annular body of porous, reticulated, open-cell polyurethane foam positioned within a cylindrical housing upon a generally disc-shaped base. The defoaming element is surrounded by a layer of woven nylon or polyester fabric, which serves as a final barrier against the passage of gaseous bubbles, as well as any solid particulate matter that may be present in the arterialized blood, to the patient. The polyurethane defoaming element is treated with an antifoam compound such as a polydimethylsiloxane compound. The arterialized blood flows radially, from the inside to the outside, through the annular element and surrounding layer of fabric and into a substantially annular defoamed blood reservoir, which includes the space between the layer of fabric and the housing and an extension of this space below the level of the generally disc-shaped base. In this known type of device, the layer of fabric surrounding the polyurethane defoaming element has heretofore been tied to the base (upon which the defoaming element is positioned) by means of a pair of nylon tie straps. Use of this tying means, however, introduces a potential problem. As defoamed blood first accumulates in the substantially annular reservoir, the possibility exists that air bubbles may be formed and trapped against the undersides of the heads of the tying straps or the straps themselves. The presence of gas bubbles downstream of the above-mentioned layer of fabric would clearly be undesirable. Additionally, it would be beneficial to improve the known type of device by providing a seal between the base and said layer of fabric that essentially eliminated any possibility of blood flow bypass around the layer of fabric and was easy to form during the manufacture of the defoaming device.

SUMMARY OF THE INVENTION

The present invention comprises a novel device for the defoaming of blood during surgical procedures comprising a porous defoaming element, a non-porous end piece in contact with a surface of the defoaming element, a layer of fabric affixed to the end piece adjacent to said surface of the defoaming element, said layer of fabric having a smaller pore size than that of the defoaming element, a blood inlet, an outlet for defoamed blood, with a blood flow path being defined through the inlet, defoaming element, layer of fabric and outlet, and a retaining ring bonded to the end piece and the layer of fabric with a portion of the layer of fabric held in a fluid-tight seal between the end piece and the ring. This fluid-tight seal acts to essentially eliminate any possibility of blood flow bypass around the layer of fabric in the vicinity of the end piece. In a preferred embodiment of the invention, the novel device includes a reservoir for storing defoamed blood, the defoamed blood outlet is at the bottom of the reservoir below the level of the end piece and the retaining ring, the retaining ring has a lowermost surface defining a boundary of the reservoir, and this lowermost surface is continuously sloped upwardly to prevent accumulation of bubbles (in blood in the reservoir) beneath said lowermost surface.

DETAILED DESCRIPTION OF THE INVENTION

The invention will be described in detail with reference to a preferred embodiment thereof, a defoaming device particularly adapted for use in conjunction with a blood oxygenator of the type disclosed in U.S. Pat. Nos. 4,065,264; 4,138,288 and 4,138,464. Reference to this embodiment does not limit the scope of the invention, which is limited only by the scope of the claims.

IN THE DRAWINGS

Figure 1:
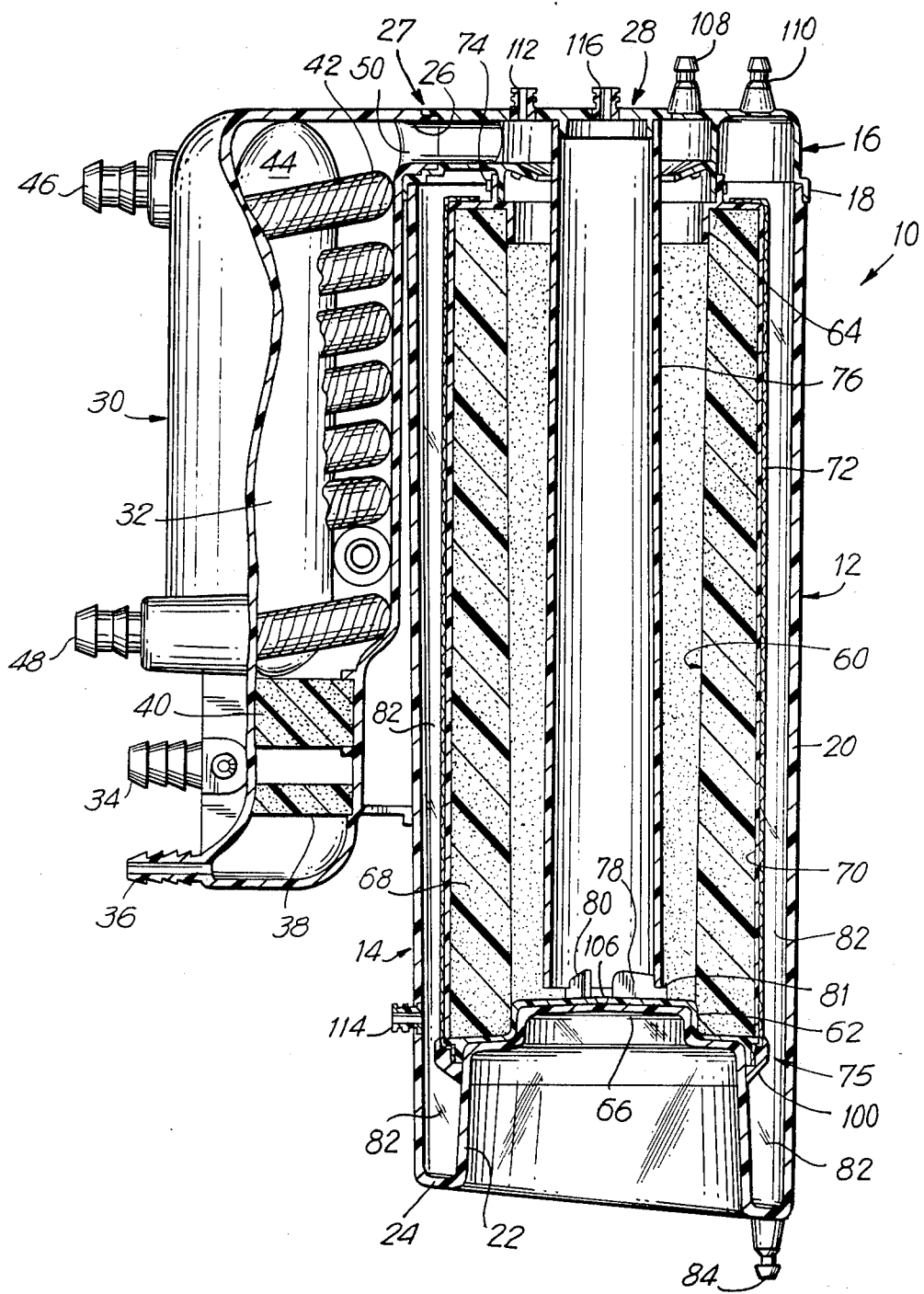
FIG. 1 is a front view of a disposable assembly of a blood oxygenator and a defoaming device of the invention, with the defoaming device shown in section and portions of the housing of the oxygenator broken away to more clearly reveal certain interior features thereof.

FIG. 1 shows a defoaming device 10 of the present invention in assembly with a "bubble-type" blood oxygenator 30 of the type disclosed in U.S. Pat. Nos. 4,065,264; 4,138,288 and 4,138,464. In the operation of the oxygenator during a surgical procedure such as a coronary bypass operation, venous blood from the patient enters an oxygenating chamber 32 in the oxygenator 30 through a blood inlet port 34. The blood is under a sufficient head of pressure to cause the blood to flow through the oxygenator. Typically, this pressure is provided by mounting the entire oxygenator/defoamer assembly below the patient. Oxygen enters an oxygen inlet port 36 and is caused to form a plurality of oxygen bubbles by means of a sparger 38. These bubbles flow through the venous blood in the area of the chamber 32 above the sparger 38. The blood and the oxygen bubbles are thoroughly admixed as they flow through a three-dimensional, open cellular mixing material 40 supported above the sparger 38 within the chamber 32 and completely filling the cross-sectional interior of the chamber along the length of the mixing material 40. The foamed, oxygenated blood then flows upward through the chamber 32 and comes into contact with a helically-ribbed heat transfer fluid tube 42, which is helically wound around a central column 44 in the chamber 32. A heat transfer fluid, such as water, enters the tube 42 through a fluid inlet port 46, and, after absorbing heat from, or transferring heat to, the blood which contacts the tube 42, exits from the tube through a fluid outlet 48. The arterialized blood rises to the top of the chamber 32 and flows through a horizontal channel 50 having a generally rectangular cross-section to the defoaming device 10 of the present invention.

Defoaming device 10 comprises a housing 12 formed by a relatively large lower cup-like portion 14, a relatively small upper cup-like portion 16 and a circular top cap 28. Portions 14 and 16 are bonded together, preferably by solvent welding, to form a circumferential seam 18. Housing 12 includes a generally cylindrical outer side wall 20, which extends above seam 18, a generally cylindrical inner wall 22 concentric with wall 20, and a ring-shaped bottom wall 24 connecting walls 20 and 22. As shown in FIG. 1, wall 20 is slightly tapered in an upward/outward fashion and wall 22 is slightly tapered in an upward/inward fashion. The tapers result from the manufacture of portion 14 by injection molding. Arterialized blood inlet 26 is provided in upper portion 16. Cap 28, which is concentric with wall 20, is bonded, preferably by solvent welding, to portion 16 of housing 12. Inlet 26 is bonded, preferably by solvent welding, to channel 50 of oxygenator 30 to form seam 27.

Defoaming device 10 also comprises a vertically-extending annular defoaming element 60, which is concentric with outer side wall 20 of housing 12. Defoaming element 60 is held between a non-porous, generally disc-shaped end piece or base 62 and an adapter 64, with the bottom surface of defoaming element 60 bonded, preferably with a hot melt adhesive, to base 62 and the top surface of defoaming element 60 in contact with adapter 64. Adapter 64 receives and is bonded, preferably by solvent welding, to a tubular projection provided in upper portion 16 of housing 12, while base 62 fits against a complimentary part 66 of lower portion 14 of housing 12 (see FIG. 1). The inner space defined within annular element 60 is in fluid communication through the top of said space and adapter 64 with inlet 26. Preferably, defoaming element 60 is made of a porous, reticulated, open-cell polyurethane foam coated with an anti-foam compound such as a polydimethylsiloxane compound and contains two annular layers 68 and 70, with the inner layer 68 being thicker and having a greater average pore size than the outer layer 70. Typically, the average pore size of inner layer 68 is from about 17 ppi (pores per inch) to about 25 ppi, while the average pore size of outer layer 70 is from about 75 ppi to about 85 ppi.

Figure 2:
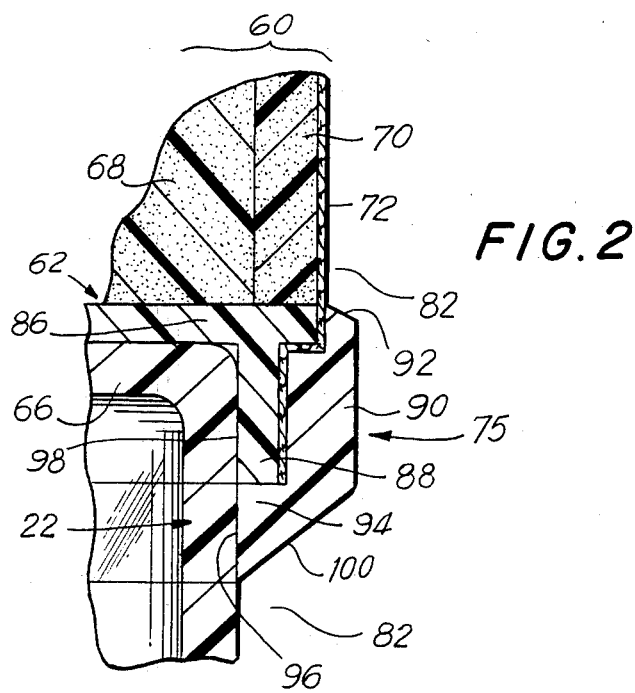
FIG. 2 is an enlarged view of a portion of FIG. 1 showing particular features of the novel defoaming device of the invention.

In the embodiment disclosed in FIGS. 1 and 2, defoaming element 60 is surrounded by an annular layer of fabric 72 having a smaller pore size than that of either layer of element 60. For example, layer 72 may be a layer of a woven nylon or polyester, e.g. polyethyleneterephthalate, fabric. Preferably, layer 72 is a layer of plain square weave polyethyleneterephthalate fabric having an average mesh opening of from about 85 microns to about 125 microns, most preferably about 105 microns. Layer 72 may be affixed to adapter 64 adjacent the top surface of element 60 with a conventional nylon tie strap 74 held within a loop sewn into the upper edge of the layer of fabric. The method of affixing the layer of fabric 72 to end piece 62 adjacent the bottom surface of element 60 with the use of retaining ring 75, which is at the heart of the present invention, will be described in detail below.

Defoaming device 10 also includes a vertically-extending non-perforated cylindrical tube 76 which is concentric with defoaming element 60 and outer side wall 20 of housing 12. At one end, tube 76 receives a tubular projection provided in cap 28. At its other end, tube 76 sits upon and is bonded, preferably by solvent welding, to a plurality of radially-extending ribs provided in end piece or base 62. In the device illustrated in FIGS. 1 and 2, three such ribs are provided. These three ribs, only two of which (78 and 80) are viewed in FIG. 1, are preferably disposed symmetrically with respect to the common longitudinal axis of tube 76 and circular end piece 62 at 120° angles (in a horizontal plane) with respect to one another. As is clearly shown in FIG. 1 with respect to rib 78, tube 76 fits within steps, e.g. 81, provided in the outer ends of the three ribs. As a result, the space within tube 76 is in fluid communication with inlet 26 and will fill with blood during the operation of device 10. Alternatively, if desired, tube 76 may be secured to base 62 in such a manner as to prevent the passage of blood from inlet 26 into tube 76.

Defoaming device 10 of the present invention includes a substantially annular reservoir 82 for receiving and temporarily storing the defoamed blood, which reservoir is generally defined by outer side wall 20 of housing 12, fabric layer 72, retaining ring 75 and inner wall 22. Bottom wall 24, which forms the bottom wall of reservoir 82, is uniformly sloped from a high point to a diametrically-opposed low point. An outlet 84 for the defoamed blood is located at this lowermost point of reservoir 82. Thus, the flow through device 10 of arterialized blood from channel 50 passes sequentially through inlet 26, adapter 64, the inner space of annular defoaming element 60, inner layer 68 of element 60, outer layer 70 of element 60, fabric layer 72, reservoir 82 and outlet 84.

Figure 3:
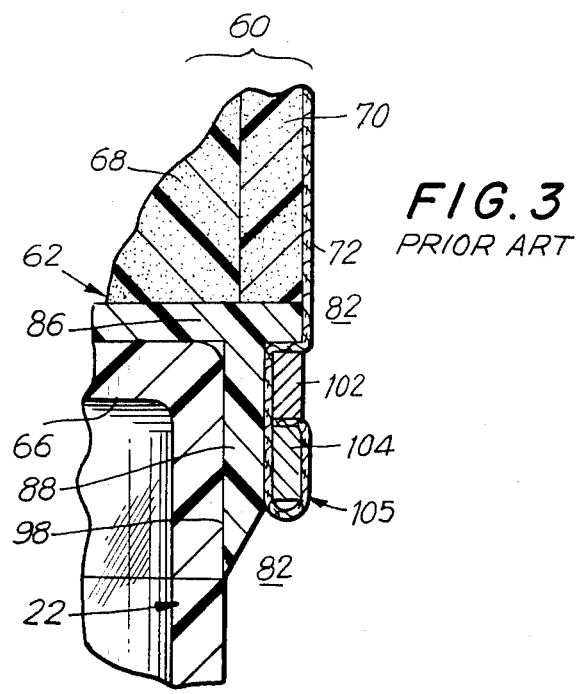
FIG. 3 is a view corresponding to FIG. 2 showing structural features of a prior art device.

The novel means of affixing fabric layer 72 to end piece 62 is illustrated in detail in FIG. 2. In the preferred configuration, end piece or base 62 includes a main body portion 86, which contacts the bottom surface of defoaming element 60, and a depending annular skirt 88 extending away from said bottom surface of element 60. As shown in FIG. 2, skirt 88 is located proximate to the periphery of body portion 86 of end piece 62 and receives the upper extremity of inner wall 22 of housing 12. Defoaming device 10 comprises an annular retaining ring 75, whose preferred cross-sectional configuration (which is complimentary to that of base 62) is illustrated in detail in FIG. 2. In this configuration, retaining ring 75 includes an annular body portion 90 adapted to fit against the outer surface of skirt 88 of base 62, an annular ring-like projection 92 extending above portion 90 which is adapted to fit against the rim of portion 86 of base 62, and a depending annular lip 94 extending beneath skirt 88. Preferably, as shown in FIG. 2, lip 94 terminates at an inner surface 96 which is coincident with the inner surface 98 of annular skirt 88. Additionally, in the preferred configuration illustrated in FIG. 2, retaining ring 75 has a lowermost surface 100 which defines part of the boundary of reservoir 82 and surface 100 is continuously sloped upwardly and radially outwardly to prevent, in the blood in reservoir 82, the accumulation of bubbles beneath said surface 100. This highly beneficial aspect of the invention can be fully appreciated by comparing FIG. 2 with FIG. 3, which shows the prior art means for affixing fabric layer 72 to end piece 62. In FIGS. 2 and 3 the same reference numerals have been used to refer to identical or similar elements. In the prior art structure of FIG. 3, fabric layer 72 is tied to base 62 by two, e.g. nylon, tie straps 102 and 104 wrapped around skirt 88. Tie 104 is held within a loop 105 sewn into the lower edge of the layer of fabric 72 while tie 102 is positioned as shown between tie 104 and the lower surface of the main body portion 86 of base 62. In this prior art configuration the possibility exists that air bubbles may be formed and trapped in the blood in reservoir 82 against the underside of strap 104 or against the underside of the head of either of the straps, particularly when the defoamed blood is first filling reservoir 82. Use of the novel structure illustrated in FIG. 2 essentially eliminates this potential problem.

Another important aspect of the present invention is that retaining ring 75 is bonded to end piece 62 and fabric layer 72 with a portion of layer 72 held in a fluid-tight seal between end piece 62 and retaining ring 75, thereby preventing bypass of blood flow around the layer of fabric 72 in the vicinity of end piece 62. This is important because the fabric layer 72 serves as a final barrier against the passage of gaseous bubbles or any solid particulate matter to the outlet 84. It is preferred to bond end piece 62, fabric layer 72 and ring 75 together by solvent welding, although any other suitable method of bonding, e.g. adhesive bonding, may be employed. Although the prior art structure shown in FIG. 3 provides a highly effective seal of fabric layer 72 to base 62, any residual possibility of blood flow bypass around layer 72 into the reservoir 82 is essentially eliminated with the utilization of the improved fixation means of the present invention. In the preferred embodiment of the invention, a portion of fabric layer 72 including the bottom edge thereof is held, as shown in FIG. 2, between projection 92 and the rim of body portion 86, between body portions 90 and 86, and between body portion 90 and skirt 88.

It is to be understood that the configuration of end piece 62 and retaining ring 75 shown in FIGS. 1 and 2 are merely exemplary and that the use of other configurations will fall within the scope of the present invention. Thus, for example, the end piece and retaining ring need not be circular in shape. As only one other alternative, the end piece may be provided with an upwardly-extending annular ring-like projection proximate to its periphery, with the retaining ring fitting against the inner surface of said projection, the bottom portion of the fabric layer being held between the ring and said projection, and the lowermost surface of the end piece being continuously sloped upwardly. Finally, it is contemplated that fabric layer 72 may be affixed at its upper end to adapter 64 by the means of the present invention (see e.g. FIG. 2) rather than with a conventional nylon tie strap.

Portions 14 and 16 and cap 28 of housing 12, adapter 64, base 62 and tube 76 are preferably made by conventional methods from a clear plastic material, most preferably a thermoplastic such as a polycarbonate. Retaining ring 75 is preferably made by conventional methods from a plastic material, most preferably a thermoplastic such as a polycarbonate. Injection molding of parts is preferred for reasons of cost. The preferred solvents for solvent welding are dichloromethane, dichloroethane and mixtures thereof. When end piece 62 and retaining ring 75 are both made of a polycarbonate and fabric layer 72 is made of a polyester, the preferred solvent for the solvent welding of end piece 62, fabric layer 72 and retaining ring 75 is dichloromethane.

The various elements of defoaming device 10 may be assembled by conventional methods. Preferably, end piece 62, fabric layer 72 and retaining ring 75 are solvent welded together after defoaming element 60 has been bonded to end piece 62 and fabric layer 72 has been positioned over element 60. Retaining ring 75 and end piece 62 are juxtaposed with fabric layer 72 held between them, and the solvent is then applied and carried along the junction of piece 62 and ring 75 by the capillary action provided by fabric layer 72. After assembly, defoaming element 60 is snugly held in compression between adapter 64 and base 62, and base 62 and ring 75 fit tightly with lower portion 14 of housing 12. However, a very small quantity of air will usually be present between base 62 and portion 14. To prevent this air from expanding and passing as a gaseous bubble or bubbles into reservoir 82 when the temperature of said air is rising (as, for example, when the patient's blood is being rewarmed at the end of a surgical procedure), a very small aperture 106 is provided in the center of base 62. Aperture 106 provides a path of low resistance so that any such expanding air will pass into tube 76 (which is upstream of element 60 and fabric layer 72) rather than reservoir 82. Since aperture 106 is made to be too small to permit significant blood flow through it during the operation of device 10, its presence is fully consistent with the characterization of base 62 as a non-porous piece, which simply means herein that the piece is of such a construction that significant blood flow through it is not permitted.

Defoaming device 10 is used in a conventional manner. The device may be primed, e.g. with sterile saline solution, through prime port 108. During operation, the blood foam is collapsed as the arterialized blood contacts defoaming element 60. The gas phase in the blood input to device 10 is thus separated from the liquid phase and flows as a single-phase gas stream through fabric layer 72 above the liquid level and then to vent 110 in upper portion 16 of housing 12. The defoamed blood passes through fabric layer 72 to reservoir 82 and outlet 84. Any gaseous bubbles that are able to pass through defoaming element 60 are stopped at fabric layer 72, coalesce, rise to the liquid surface while remaining upstream of layer 72 and join the gas stream flowing through layer 72 to vent 110. Defoaming device 10 may be provided with one or more blood sampling ports, e.g. 112 and 114, medicament dispensing ports, e.g. 116, temperature probe ports (e.g. a temperature probe port not shown in FIG. 1 proximate to outlet 84), and other similar conventional attachments.

We claim:

1. In a device for the defoaming and storing blood during surgical procedures comprising:
   a vertically-extending porous annular defoaming element defining an inner space and having substantially ring-shaped top and bottom surfaces;
   a non-porous, generally disc-shaped base in contact with, and substantially concentric with, the bottom surface of said defoaming element;
   an annular layer of fabric surrounding the defoaming element and affixed to the base adjacent to the bottom surface of the defoaming element, said layer of fabric having a smaller pore size than that of the defoaming element;

a blood inlet in communication with said inner space;

an outlet for defoamed blood, with a blood flow path being defined by the inlet, defoaming element, layer of fabric and outlet being in fluid communication with each other in series;

an annular retaining element, substantially concentric with said defoaming element, secured to the base, an inner wall and the layer of fabric, with a portion of the layer of fabric held in a fluid-tight seal between the base and the retaining element, thereby preventing bypass of blood flow around the layer of fabric;

a housing including a top wall, said inner wall and a generally cylindrical outer side wall spaced from said layer of fabric;

a reservoir for storing defoamed blood, a portion of which is defined by said layer of fabric, the adjacent outer side housing wall and sail inner wall, with said reservoir extending below the level of the base and the retaining element and the defoamed blood outlet being at the bottom of said reservior; and a gas vent in the top wall of the housing in communication with said reservoir, the improvement comprising said annular retaining element being a flexurally rigid annular retaining ring bonded to said base and said layer of fabric by solvent welding or adhesive bonding, with said annular retaining ring having a generally ring-shaped lower surface defining a boundary of said reservoir, said lower surface being continuously sloped upwardly and radially outwardly across its entire radial thickness to prevent accumulation of bubbles beneath said lower surface.

2. A device of claim 1 wherein the improvement further comprises a depending annular skirt proximate to the circumferential periphery of said generally disc-shaped base and extending downwardly away from said bottom surface of the defoaming elements, and the retaining ring, which receives and is bonded to said skirt with a portion of the layer of fabric held in a fluid-tight seal between the skirt and the ring.

3. In a device for the defoaming and storing blood during surgical procedures comprising:

a vertically-extending porous annular defoaming element having substantially ring-shaped top and bottom surfaces and defining a substantially cylindrical inner space having a top and a bottom;

a blood inlet in communication with said inner space through the top of said space;

a non-porous, generally disc-shaped base in contact with, and substantially concentric with, the bottom surface of said defoaming element and preventing blood flow through the bottom of said inner space, said base including an annular downwardly-extending skirt proximate to be circumferential periphery of said base and said annular skirt having substantially cylindrical inner and outer surfaces;

an annular layer of fabric surrounding the defoaming element and affixed to the base adacent to the bottom surface of the defoaming element, said layer of fabric having a smaller pore size than that of the defoaming element;

an annular retaining element, substantially concentric with said defoaming element, receiving said skirt and secured to the skirt and the layer of fabric with a portion of said layer of fabric held in a fluid-tight seal between the skirt and the retaining element, thereby preventing bypass of blood flow around the layer of fabric;

a housing including a top wall comprising said blood inlet, a generally cylindrical outer side wall and a generally cylindrical inner wall extending downwardly from said base, with a reservoir for defoamed blood being defined generally by the outer side wall, the layer of frabric, the retaining element and the inner wall, said annular shirt and said annular retaining element being secured to said inner wall;

a gas vent in the top wall of the housing in communication with said reservoir; and a defoamed blood outlet at the bottom of said reservoir, the improvement comprising said annular retaining element being a flexurally rigid annular retaining ring bonded to said base and said layer of fabric by solvent welding or adhesive bonding, with said annular retaining ring having a generally ring-shaped lower surface defining a boundary of said reservoir, said lower surface being continuously sloped upwardly and radially outwardly across its entire radial thickness to prevent accumulation of bubbles beneath said lower surface.

4. A device of claim 3 wherein the improvement further comprises said retaining ring, which includes an annular body portion which fits against the outer surface of said annular skirt, and an annular lip extending radially inwardly, beneath said annular skirt, so that both the inner surface of the annular skirt and the inner surface of the annular lip abut the outer surface of said inner wall.

5. A device of claim 3 wherein the improvement further comprises said annular layer of fabric, which has substantially circular top and bottom edges, and said annular skirt, which has a circular bottom edge, wherein a portion of said layer of fabric terminates at the bottom edge of said skirt.

* * * * *